United States Patent [19]

Sakurai et al.

[11] Patent Number: 5,425,704
[45] Date of Patent: Jun. 20, 1995

[54] APPARATUS FOR GENERATING ULTRASONIC OSCILLATION

[75] Inventors: Tomohisa Sakurai, Hachioji; Masakazu Gotanda, Tsukui, both of Japan

[73] Assignee: Olympus Optical Co., Ltd., Tokyo, Japan

[21] Appl. No.: 895,839

[22] Filed: Jun. 9, 1992

Related U.S. Application Data

[62] Division of Ser. No. 513,230, Apr. 23, 1990, Pat. No. 5,151,085.

Foreign Application Priority Data

Apr. 28, 1989 [JP] Japan .................. 1-107788
May 15, 1989 [JP] Japan .................. 1-120958

[51] Int. Cl.$^6$ .................. A61B 17/22; A61B 17/32
[52] U.S. Cl. .................. 604/22; 601/2; 606/169; 606/128; 310/316
[58] Field of Search .................. 128/24 AA, 660.01; 604/22; 606/169-171; 310/313 R, 314-317

[56] References Cited

U.S. PATENT DOCUMENTS

| | | | |
|---|---|---|---|
| 3,746,897 | 7/1973 | Karatjas | 310/316 |
| 4,181,864 | 1/1980 | Etzold | 310/316 |
| 4,583,529 | 4/1986 | Briggs | 128/24 AA |
| 4,703,213 | 10/1987 | Gäsler | 310/316 |
| 4,705,038 | 11/1987 | Sjostrom et al. | 604/22 |
| 4,768,496 | 9/1988 | Kreizman et al. | 128/24 AA |
| 4,966,131 | 10/1990 | Houghton et al. | 128/24 AA |
| 4,970,656 | 11/1990 | Lo et al. | 310/316 |
| 4,973,876 | 11/1990 | Roberts | 310/316 |
| 5,026,387 | 6/1991 | Thomas | 128/24 AA |
| 5,042,460 | 8/1991 | Sakurai et al. | 128/24 AA |
| 5,151,085 | 9/1992 | Sakurai et al. | 128/24 AA |
| 5,180,363 | 1/1993 | Idemoto et al. | 128/24 AA |

FOREIGN PATENT DOCUMENTS

| | | |
|---|---|---|
| 63-162086 | 7/1988 | Japan . |
| 63-212341 | 9/1988 | Japan . |
| 63-212342 | 9/1988 | Japan . |

*Primary Examiner*—Krista M. Pfaffle
*Attorney, Agent, or Firm*—Stevens, Davis, Miller & Mosher

[57] ABSTRACT

The apparatus includes an ultrasonic transducer having a hand piece, an ultrasonic vibrating element secured to the hand piece and a probe coupled with the hand piece for propagating the ultrasonic oscillation produced by the ultrasonic vibrating element, a driving circuit for producing a driving signal for the ultrasonic vibrating element, a voltage controlled amplifier for amplifying the driving signal, an impedance matching transformer having a plurality of primary windings connected to the output of the voltage controlled amplifier via a switching circuit and a secondary winding connected to the ultrasonic vibrating element, a probe identification circuit for detecting the probe connected to the hand piece to produce a probe identification signal, a feedback control loop for generating a control voltage which is applied to the voltage controlled amplifier for controlling the amplification factor thereof in accordance with a driving current of the driving signal, an impedance detecting circuit for detecting the impedance of the ultrasonic transducer and controlling, the switching circuit such that a given primary winding is connected to attain the impedance matching between the driving circuit and the ultrasonic transducer, and a voltage limiter arranged in the feedback control loop such that the maximum value of the control voltage is limited in accordance with the probe identification signal.

22 Claims, 15 Drawing Sheets

FIG_1A
*PRIOR ART*
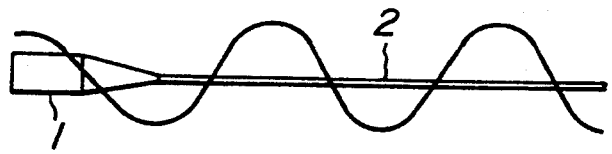
FIG_1B
*PRIOR ART*
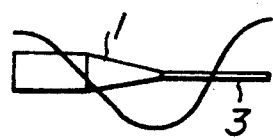

FIG_5A
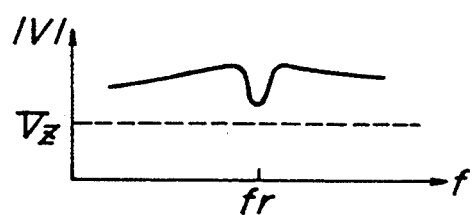
FIG_5B
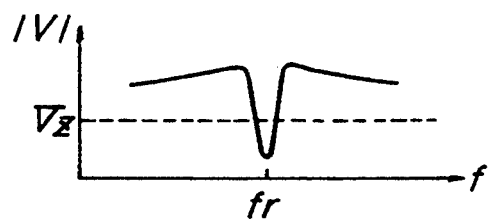

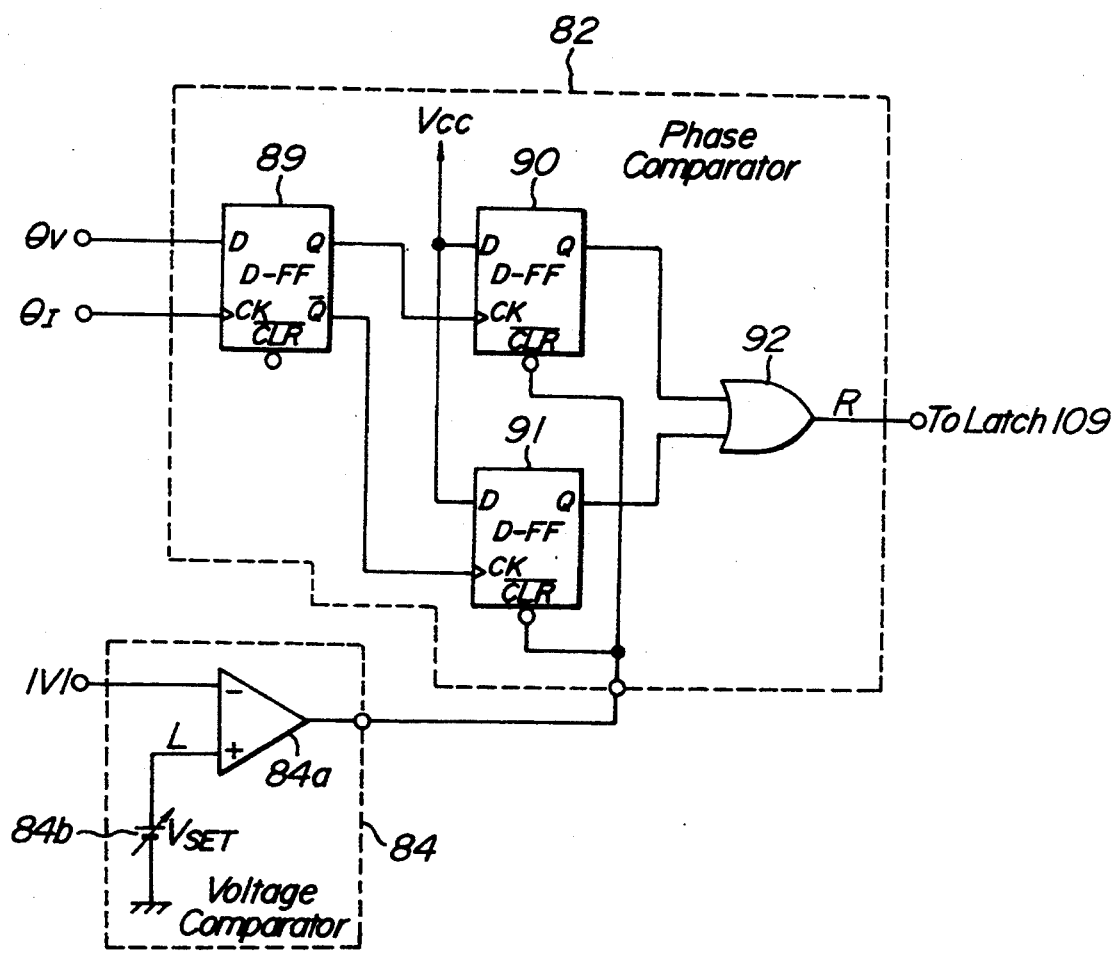
FIG_8

FIG_12

FIG_14

FIG_16
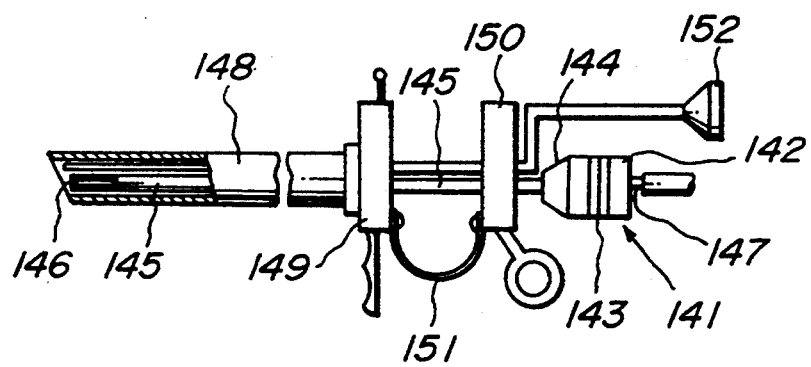

APPARATUS FOR GENERATING ULTRASONIC OSCILLATION

This is a division of application Ser. No. 07/513,230, filed Apr. 23, 1990, now U.S. Pat. No. 5,151,085.

BACKGROUND OF THE INVENTION

FIELD OF THE INVENTION AND RELATED ART STATEMENT

The present invention relates to an apparatus for generating an ultrasonic oscillation, and more particularly to an apparatus for generating an ultrasonic oscillation comprising an ultrasonic transducer having an ultrasonic vibrating element for producing an ultrasonic oscillation and a probe for transmitting the oscillation produced by the ultrasonic vibrating element, and a driving circuit for supplying a driving signal to the ultrasonic vibrating element.

Heretofore, there have been proposed various kinds of apparatuses using the ultrasonic transducer.

For instance, ultrasonic surgical knives and ultrasonic working machines have been developed. In these ultrasonic apparatuses, it is advantageous to effects the impedance matching between the ultrasonic transducer and, the driving circuit in order to improve the driving efficiency of the ultrasonic vibrating element.

FIGS. 1A and 1B show the known ultrasonic probe in which vibrating rods 2 and, 3 having different lengths are detachably secured to an ultrasonic transducer 1. The inventor of the instant application has experimentally confirmed that the impedance of the probe illustrated in FIG. 1B is smaller than that of the probe depicted in FIG. 1A by about five times. Therefore, when these probes are driven by the same driving circuit, if the output impedance of the driving circuit is fixedly matched to either one of the vibrating rods 2 and 3, the impedance matching could not be attained for the other of the vibrating rods 3 or 2 and the driving efficiency of the ultrasonic vibrating element 1 would be decreased to a great extent.

In order to mitigate the above mentioned drawback, in a Japanese Patent Laid-open Publication Kokai Sho 63-162086, there has been proposed an ultrasonic transducer in which taps on a secondary side of a coupling transformer for electromagnetically coupling the ultrasonic vibrating element and the driving circuit are switched in accordance with the amplitude of the oscillation or vibration of the ultrasonic vibrating element.

However, in the ultrasonic oscillation generating apparatus disclosed in said Japanese Patent Laid-open Publication Kokai Sho 63-162086, there is a problem that the impedance matching could be no more attained due to the fact that the adjustment of the impedance matching is carried out on the basis of the amplitude of the oscillation. That is to say, in the ultrasonic transducer the amplitude of the oscillation is proportional to an amplitude of a current passing through the ultrasonic vibrating element, so that if the impedance of the transducer circuit is increased twice, the taps on the secondary side of the coupling transformer are changed such that the voltage applied to the ultrasonic vibrating element is increased also twice in order to keep the amplitude of the current unchanged. Then, the impedance of the transducer circuit viewed from the primary side of the transformer is decreased by four times, because the ratio of the primary winding to the secondary winding becomes 1:2. This results in that the impedance of the load for the driving circuit is decreased by two times, although the impedance of the transducer circuit is increased by two times. Therefore, the impedance matching could not be attained and the ultrasonic vibrating element could not be driven efficiently.

Further, in the known ultrasonic generating apparatus, the taps are provided on the secondary side of the coupling transformer, i.e. on the vibrating element side of the transformer. When the apparatus is applied to the ultrasonic surgical knife, a switching circuit for switching the secondary winding portions is arranged in the circuitry on the patient side, so that the electrical insulation should be effected to a very high degree in order to achieve the protection against the electric leakage and discharge. This apparently increases the cost of the apparatus.

In order to attain a proper impedance matching, it would be also considered that the impedance of ultrasonic transducers to be used are previously measured and when an ultrasonic transducer is used, the impedance matching is attained manually in accordance with the measured impedance of the relevant transducer. In such a solution, there might be produced another problem of the misoperation of the user and the driving circuit might be broken under the overload condition.

In Japanese Patent Laid-open Publication Kokai Sho 63-212341 and 63-212342, there are described further known ultrasonic apparatuses in which objects such as hematoma and tumor produced within a patient body are broken into pieces by irradiating the ultrasonic beam thereupon by inserting the ultrasonic endoscope and pieces of the objects are sucked out of the body via a tube arranged in the endoscope. In such ultrasonic surgical operating apparatus, it is desired that the amplitude of the ultrasonic probe driven by the ultrasonic vibrating element is kept constant regardless of the acoustic impedance of the objects. As explained above, since the amplitude of the ultrasonic vibrating element is proportional to the amplitude of the current passing through the element, the output of the oscillator in the driving circuit is supplied to the vibrating element via a voltage controlled amplifier (VCA) whose amplification factor can be changed by a control voltage, and the amplification factor of the VCA is adjusted in accordance with the driving current such that the driving current can be kept constant.

In the above mentioned ultrasonic apparatus in which the ultrasonic vibrating element is driven by the constant current circuit, the construction of the apparatus can be made simple and the amplitude of the ultrasonic oscillation can be maintained substantially constant. However, the electric stability of the known apparatus sometimes becomes deteriorated. For example, in the above explained ultrasonic surgical apparatus, when the tip of the ultrasonic probe is urged against the object, the electric property of the probe is changed to a large extent in accordance with the objects and the amplitude of the driving current becomes extremely small. Then, the constant current circuit operates such that the control voltage for the VCA is abnormally increased and the voltage applied to the ultrasonic vibrating element becomes larger than threshold voltages of the element and driving circuit, so that they might be broken. This is quite dangerous for the patient.

SUMMARY OF THE INVENTION

The present invention has for its object to provide a novel and useful apparatus for generating the ultrasonic oscillation in which the above mentioned drawbacks of the known apparatuses can be removed and the impedance matching between the ultrasonic vibrating element and the driving circuit can be always attained correctly in an automatic manner and the ultrasonic vibrating element can be driven always efficiently.

It is another object of the present invention to provide an apparatus for generating the ultrasonic oscillation in which the ultrasonic vibrating element can be always driven stably without damaging the driving circuit and element as well as without damaging or injuring the patient.

According to the invention, an apparatus for generating an ultrasonic oscillation comprises:
- an ultrasonic transducer having an ultrasonic vibrating element for producing an ultrasonic oscillation and a probe for transmitting the ultrasonic oscillation produced by the ultrasonic vibrating element;
- a driving circuit for supplying a driving signal to said ultrasonic vibrating element:
- an impedance matching means connected between said ultrasonic transducer and said driving circuit for matching the output impedance of the driving circuit to the impedance of said ultrasonic transducer;
- an impedance detecting means for detecting the impedance of said ultrasonic transducer to generate an impedance detecting signal; and
- controlling means for automatically controlling said impedance matching means in accordance with said impedance detection signal supplied from said impedance detecting means such that the output impedance of said driving circuit is matched to the impedance of said ultrasonic transducer.

In a preferred embodiment of the apparatus according to the invention, said impedance matching means comprises a matching transformer having a plurality of primary windings and a secondary winding connected to the ultrasonic transducer, a switching circuit for selectively connecting one of said primary windings to the driving circuit, and a control circuit for controlling said switching circuit in accordance with said impedance detection signal supplied from said impedance detecting means such that the output impedance of said driving circuit is matched with the impedance of According to further aspect of the invention, an apparatus for generating an ultrasonic oscillation comprises:
- an ultrasonic transducer having an ultrasonic vibrating element for producing an ultrasonic oscillation and a probe for transmitting the ultrasonic oscillation produced by the ultrasonic vibrating element;
- a driving circuit for supplying a driving signal to, said ultrasonic vibrating element;
- an impedance matching means connected between said ultrasonic transducer and said driving circuit for matching the output impedance of the driving circuit to the impedance of said ultrasonic transducer;
- a probe identifying means for identifying a kind of said ultrasonic transducer to generate a probe identification signal; and
- controlling means for automatically controlling said impedance matching means in accordance with said probe identification signal supplied from said probe identifying means such that the output impedance of said driving circuit is matched to the impedance of said ultrasonic transducer.

According to another aspect of the invention, an apparatus for generating an ultrasonic oscillation comprises:
- an ultrasonic transducer having an ultrasonic vibrating element for producing an ultrasonic oscillation and a probe for transmitting the oscillation produced by the ultrasonic vibrating element:
- a driving circuit having a voltage controlled amplifier for supplying a driving power to said ultrasonic vibrating element;
- a feedback loop connected between said ultrasonic transducer and said driving circuit for detecting a current of said driving power supplied to said ultrasonic transducer and applying a control voltage corresponding to said current of the driving power to said voltage controlled amplifier to control an amplification factor of the voltage controlled amplifier; and
- a voltage limiting means connected in said feedback loop for limiting an amplitude of said control voltage.

According to still another aspect of the invention, an apparatus for generating an ultrasonic oscillation comprises:
- an ultrasonic transducer having an ultrasonic vibrating element for producing an ultrasonic oscillation and a probe for transmitting the ultrasonic oscillation produced by the ultrasonic vibrating element;
- a driving circuit having a voltage controlled amplifier for supplying a driving power to said ultrasonic vibrating element;
- a feedback loop connected between said ultrasonic transducer and said driving circuit for detecting a current of said driving power supplied to said ultrasonic transducer and applying a control voltage corresponding to said current of the driving power to said voltage controlled amplifier to control an amplification factor of the voltage controlled amplifier;
- voltage limiting means having a plurality of voltage limiting elements connected in said feedback loop for limiting an amplitude of said control voltage;
- probe identifying means for identifying a kind of said ultrasonic transducer to generate a probe identification signal; and
- controlling means for automatically switching said plurality of voltage limiting elements of the voltage limiting means in accordance with the probe identification signal produced by the probe identifying means.

BRIEF DESCRIPTION OF THE DRAWINGS

FIGS. 1A and 1B are schematic views showing the vibration mode of the known ultrasonic oscillation generating circuit;

FIGS. 5A and 5B are graphs showing the frequency characteristic of the driving voltage;

FIG. 8 is a block diagram showing the construction of the phase comparator;

FIG. 16 is a side view depicting the whole construction.

DESCRIPTION OF THE PREFERRED EMBODIMENTS

EMBODIMENTS

Figure 2:
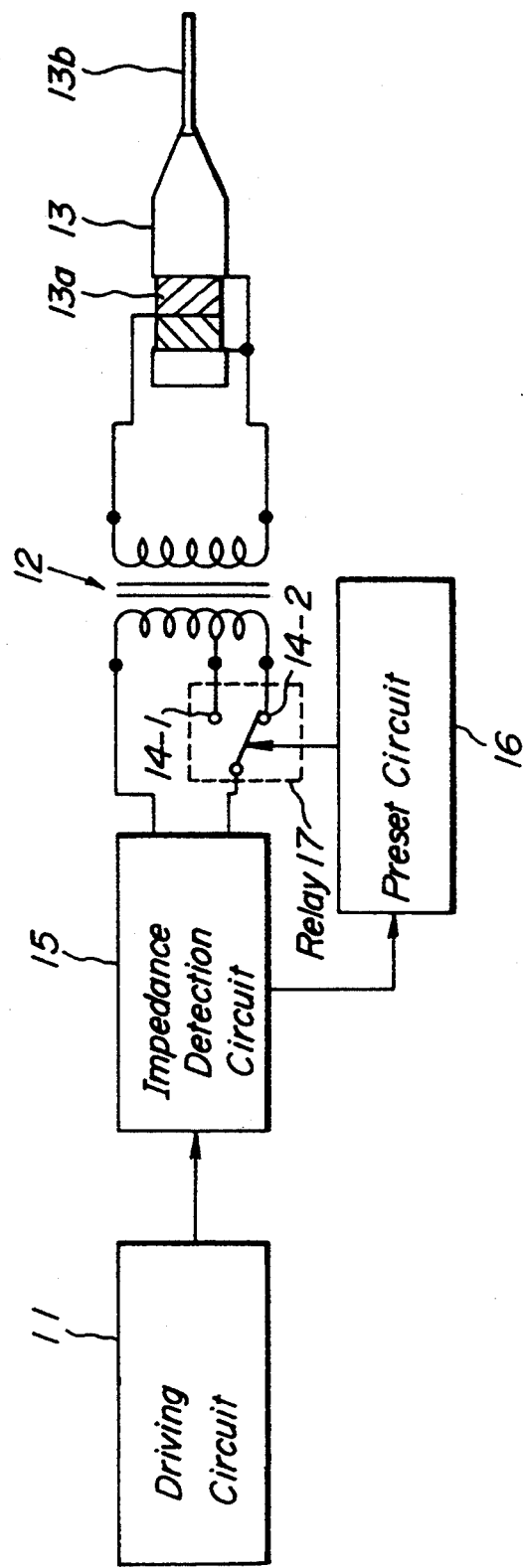
FIG. 2 is a block diagram illustrating the principal construction of the ultrasonic oscillation generating apparatus according to the invention.

FIG. 2 shows the principal construction of the apparatus for generating the ultrasonic oscillation according to the invention. An output signal generated from a driving circuit 11 is supplied via a matching transformer 12 which serves as a variable matching means for an ultrasonic transducer or probe 13 including ultrasonic vibrating element 13a and vibrating rod 13b. The matching transformer 12 comprises taps 14-1 and 14-2 provided on the primary side of the transformer for changing the number of winding turns. To the primary side of the transformer 12 is connected an impedance detection circuit 15 for detecting the impedance of the ultrasonic transducer 13. In accordance with the impedance of the ultrasonic transducer 13 detected by the impedance detection circuit 15, a controlling means comprising a preset circuit 16 and a relay 17 is driven such that the output impedance of the driving circuit 11 is changed by changing the taps 14-1 and 14-2 to attain the optimum condition for the ultrasonic transducer 13. In this manner, the matching between the driving circuit 11 and the ultrasonic transducer 13 can be attained in an automatic manner, so that the ultrasonic vibrating element 13a can be always driven efficiently.

By constructing the apparatus in the manner explained above, the impedance of the ultrasonic transducer 13 can be always correctly matched to the impedance of the driving circuit 11 in an automatic manner, so that the ultrasonic transducer can be driven in a very efficient manner.

Figure 3:
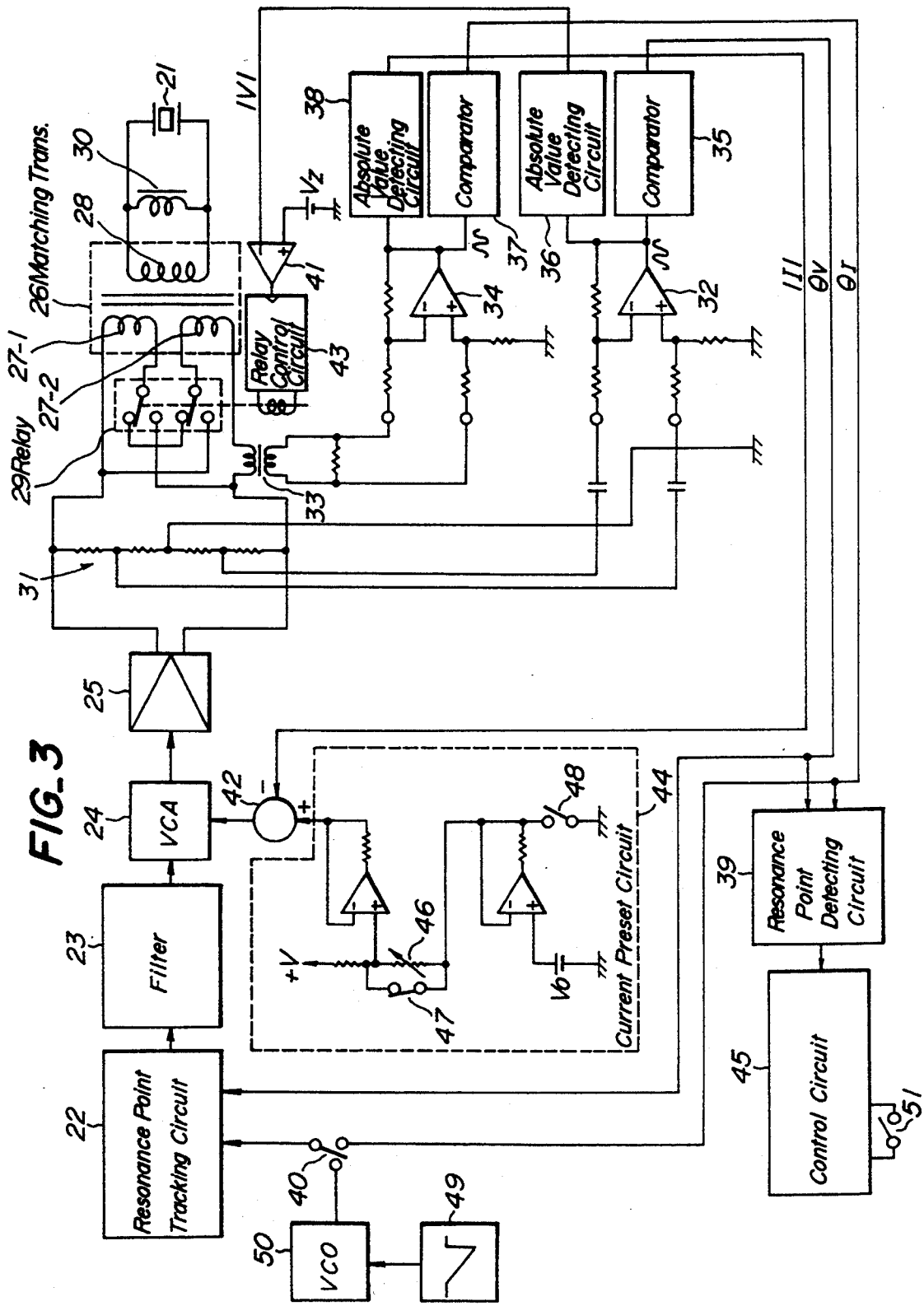
FIG. 3 is a block diagram depicting a first embodiment of the ultrasonic oscillation generating apparatus according to the invention.

FIG. 3 is a block diagram showing a first embodiment of the ultrasonic oscillation generating apparatus according to the invention in the present embodiment, voltage phase and current phase of a driving signal for the ultrasonic transducer comprising an ultrasonic vibrating element 21 are detected, and the frequency of the driving signal is automatically controlled to be equal to a resonance frequency of the ultrasonic vibrating element by a resonance point tracking circuit 22 in accordance with the detected voltage and current phases. That is to say, the so-called phase lock loop control is effected.

An output signal from the resonance point tracking circuit 22 is supplied to a filter 23 and is converted into a driving signal having a sinusoidal waveform. Then, the driving signal is supplied via a voltage controlled amplifier (VCA) 24 whose amplification factor can be controlled and a power amplifier 25 to a primary side of a matching transformer 26. The matching transformer 26 includes two primary windings 27-1 and 27-2 and a secondary winding 28. The two primary windings 27-1 and 27-2 may be connected in series or in parallel with each other by means of a relay 29. To the secondary winding 28 are connected the ultrasonic vibrating element 21 and a compensating inductor 30 for canceling the damping capacitance of the element 21. It should be noted that in the present embodiment the ratio of turns of the windings 27-1, 27-2 and 28 is set to 1:1:2 so that the ratio of the primary and secondary windings may changed between 1:1 and 1:2.

The voltage applied to the ultrasonic vibrating element 21 via the power amplifier 25 is detected by a potentiometer 31 connected in parallel, with the primary side of the matching transformer 26, and an output of the potentiometer 31 is applied to a differential amplifier 32 to remove in-phase noise contained therein. The current passing through the ultrasonic vibrating element 71 is detected by a current sensor 33 connected in series with the primary side the matching transformer 26 and the detected signal is supplied to a differential amplifier 34 to remove in-phase noise contained therein.

The voltage detection signal generated by the differential amplifier 32 is supplied to a comparator 35 to detect a voltage phase signal $\theta_V$ and is also supplied to an absolute value detecting circuit 36 to derive an absolute value of the detected voltage $|V|$. Similarly, the current detection signal generated from the differential amplifier 34 is supplied to a comparator 37 to produce a current phase signal $\theta_1$ and is supplied to an absolute value detecting circuit 38 to derive an absolute value of the detected current $|I|$.

The voltage phase signal $\theta_V$ produced from the comparator 35 is supplied to a resonance point tracking circuit 22 as well as to a resonance point detecting circuit 39 for detecting the resonance point by sweeping the frequency of the driving signal, which will be explained later. The current phase signal $\theta_1$ produced by the comparator 37 is supplied to the resonance point detecting circuit 39 as well as to the resonance point tracking circuit 22 via a switch 40. The absolute value $|V|$ of the voltage detection signal generated by the absolute value detecting circuit 36 is supplied to one input of a voltage comparator 41 and the absolute value $|I|$ of the current detection signal generated by the absolute value detecting circuit 38 is supplied to one input of a differential amplifier 42. To the other input of the differential amplifier 41 is applied a predetermined preset voltage $V_Z$ and a difference between the absolute value $|V|$ and the preset value $V_Z$ is latched by a relay control circuit 43 to control the relay 29. To the other input of the differential amplifier 42 is applied a preset current signal from a current preset circuit 44 to detect a difference between the absolute value $|I|$ of the current detection signal and the preset current value. The amplification factor of the VCA 24 is controlled by the output signal of the differential amplifier 42 such that the difference becomes zero, so that the ultrasonic vibrating element 21 can be driven with the constant current corresponding to the preset current value. It should be noted that the output of the resonance point detecting circuit 39 is supplied to a control circuit 45.

The current preset circuit 44 comprises means for generating a reference voltage $V_O$ for presetting the low constant current during the start time period, a variable resistor 46 for presetting a constant current for driving the ultrasonic vibrating element 21 at a predetermined amplitude in the resonance point tracking mode, a switch 47 for connecting or disconnecting the variable resistor 46, and a switch 48 for forcedly stopping the vibration of the ultrasonic vibrating element 21 by making the control voltage applied to VCA 24 zero.

In order to sweep the frequency of the driving signal for the ultrasonic vibrating element 21, there is provided a generator 49 for generating the sawtooth signal and the sawtooth signal is supplied to a voltage controlled oscillator (VCO) 50 to generate a reference sweep signal having a linearly varying frequency. The reference sweep signal thus produced is supplied to the resonance point tracking circuit 22 via the switch 40. It should be noted that the switch 40, relay control circuit 43, switches 47, 48, generator 49 and other circuits are controlled by the control circuit 45. Further, to the control circuit 45 is connected a switch 51 for actuating and stopping the apparatus.

Figure 4:
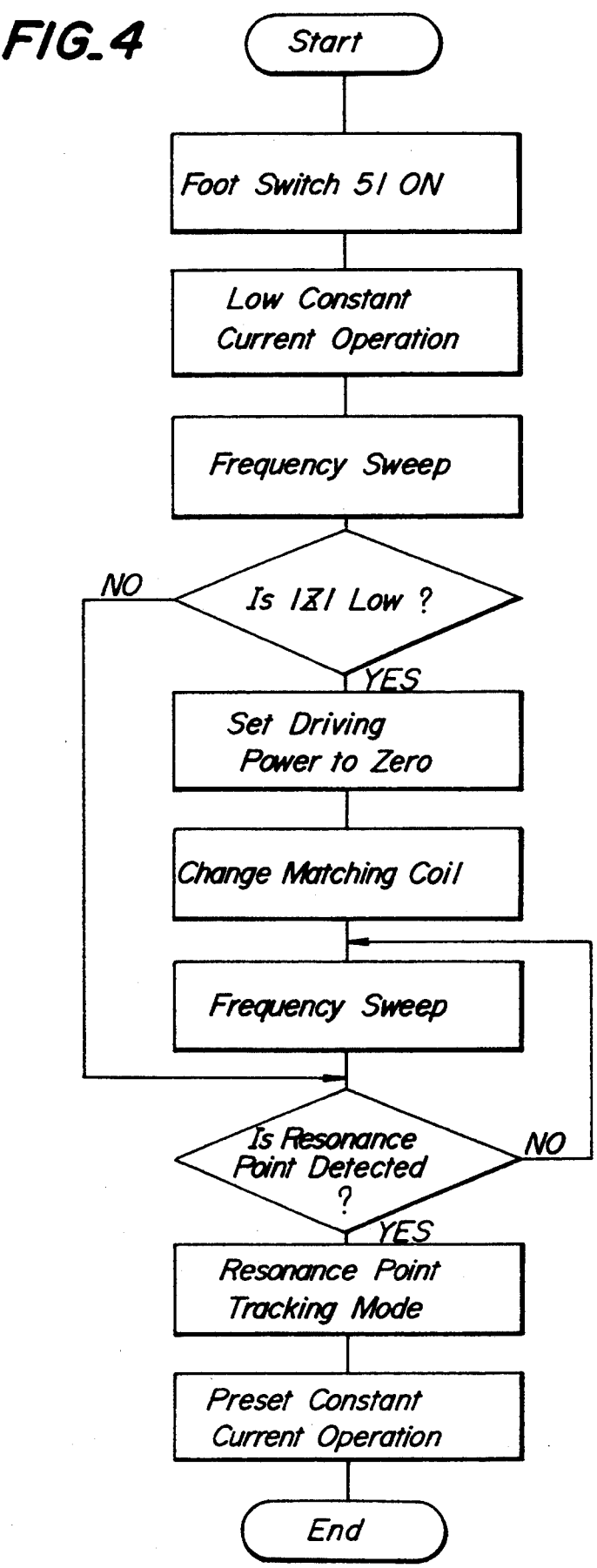
FIG. 4 is a flow chart for explaining the generation of the apparatus shown in FIG. 3.

Now the operation of the apparatus of this embodiment will be explained also with reference to a flow chart shown in FIG. 4.

While the switch 51 is made off, the switch, 40 is connected to VCO 50, and switches 47 and 48 are made on and off, respectively. Moreover the winding ratio of the primary and secondary sides of the matching transformer 26 is set to 1:1. When the switch 51 is made on, the ultrasonic vibrating element 21 is driven at the low constant current set by the reference voltage $V_O$ of the current preset circuit 44, and further the generator 49 is actuated to control VCO 50 and the frequency of the driving signal is swept in accordance with the reference sweep signal generated from VCO 50. That is to say, the resonance point tracking circuit 22 is locked to the output from VCO 50 and the oscillation frequency of the PLL is scanned by scanning the output frequency of VCO 50 in accordance with the output of the generator 49.

During the above mentioned frequency scan, the ultrasonic vibrating element 21 is driven at the constant current mode owing to the operation of the current preset circuit 44, differential amplitude 42 and VCA 24. Therefore, if the constant current is set $|I_O|$, the impedance $|Z|$ can be detected by monitoring the voltage $|V|$ from the following equation:

$$|Z| = \frac{1}{|I_O|} \cdot |V|$$

The impedance $|Z|$ becomes minimum at the resonance point $f_r$ during the frequency sweep, so that the voltage $|V|$ also becomes minimum at the resonance point $f_r$ as shown in FIGS. 5A and 5B which correspond to the $|V|$ property of the ultrasonic transducer illustrated in FIGS. 1A and 1B. Therefore, by comparing $|V|$ with the preset voltage $V_Z$ in the comparator 41, it can be detected that the ultrasonic transducer having the small impedance connected when the comparator 41 generates the output signal during the scan, and the ultrasonic transducer having the large impedance is connected when the comparator 41 does not generate the output signal.

When it is detected that the impedance $|Z|$ of the ultrasonic transducer is large, the switch 48 is made on to set the control voltage for VCA 24 to zero to stop the Output of the power amplifier 25. In this condition, the relay 29 is actuated in accordance with the impedance detection result latched in the relay control circuit 43 and the ratio of the windings of the matching transformer 26 is changed to 1:2. In this manner, the output impedance of the driving circuit is matched to the impedance of the ultrasonic transducer connected to the driving circuit, After that, the switch 48 is made off and the generator 49 is actuated again to scan the driving frequency for the ultrasonic vibrating element 21 in accordance with the reference sweep signal, and the resonance point is detected by the resonance point detection circuit 39 in accordance with the voltage phase signal $\theta_V$ and current phase signal $\theta_1$. At the resonance point, the phase difference between these phase signals becomes zero.

After the resonance point has been detected, the switch 40 is connected to the comparator 37 to lock the resonance point tracking operation. When the tracking is locked, the switch 47 is made off and the ultrasonic vibrating element 21 is driven at the current value set by the variable resistor 46.

When it is detected that the ultrasonic transducer has the small impedance $|Z|$ and the winding ratio of the matching transformer 26 may be remained 1:1, the resonance point is detected during this frequency scan, so that the rescan is not effected and the switch 40 is connected to the comparator 37 after the resonance point has been detected to enter into the lock in mode.

As explained above, in the present embodiment, the dynamic impedance of the ultrasonic vibrating element 21 is detected to automatically corrected the impedance matching, and thus the error in the manual matching can be effectively avoided and the ultrasonic transducer can be driven always efficiently even if the impedance of the probe connected to the ultrasonic vibrating element is changed to a great extent. In this manner, the ultrasonic apparatus such as the ultrasonic surgical knife and ultrasonic working machine can be driven efficiently. Further the impedance matching is effected by charging the taps on the primary side of the matching transformer, so that when the apparatus is applied to the medical devices such as the ultrasonic surgical knife, it is not necessary to include the switching circuits and control circuits in the circuit on the patient side and the patient can be protected against the danger such as the breakage of insulation and leakage.

Figure 6A:
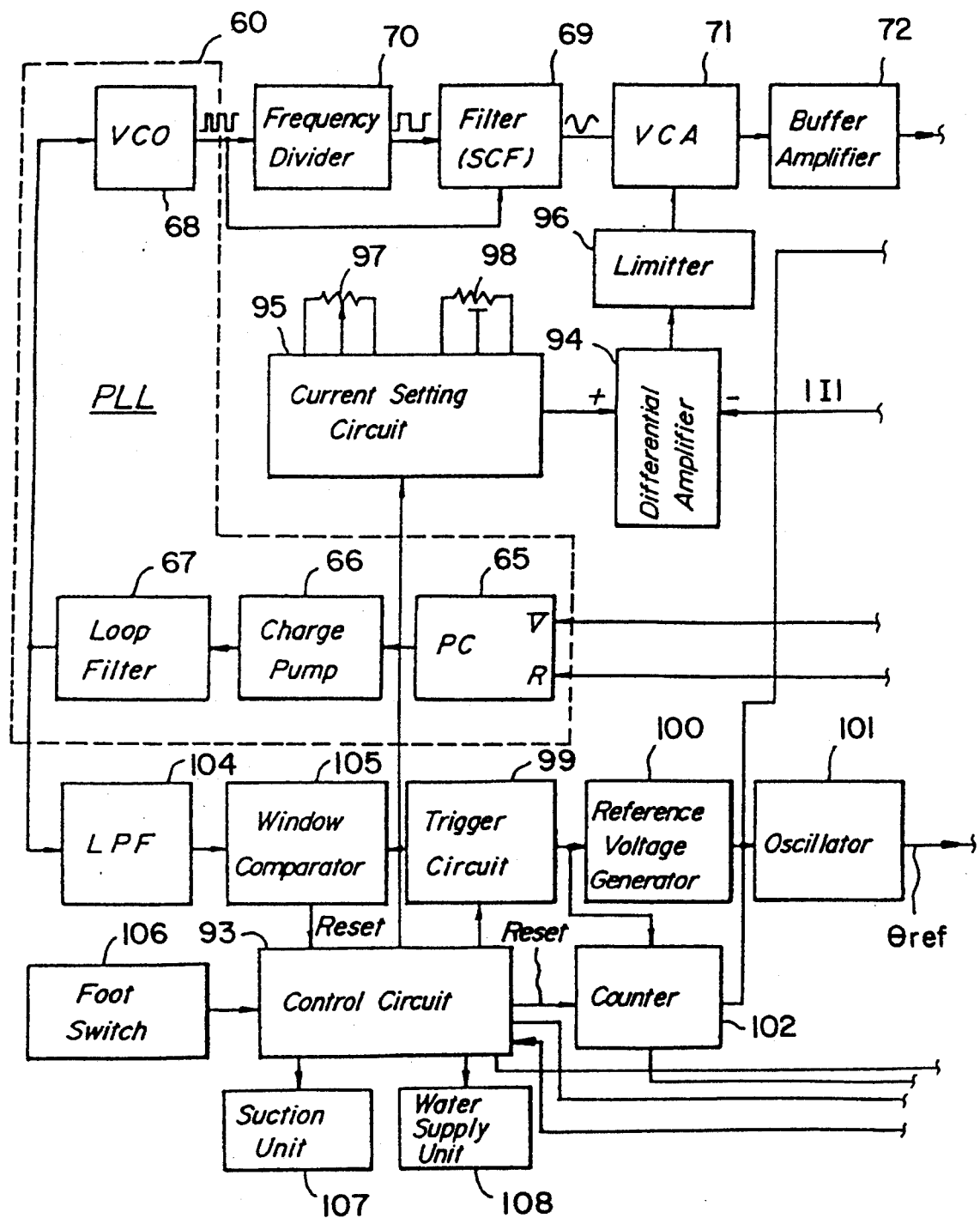
FIGS. 6A and 6B are a block diagram illustrating a second embodiment of the apparatus according to the invention.
Figure 6B:
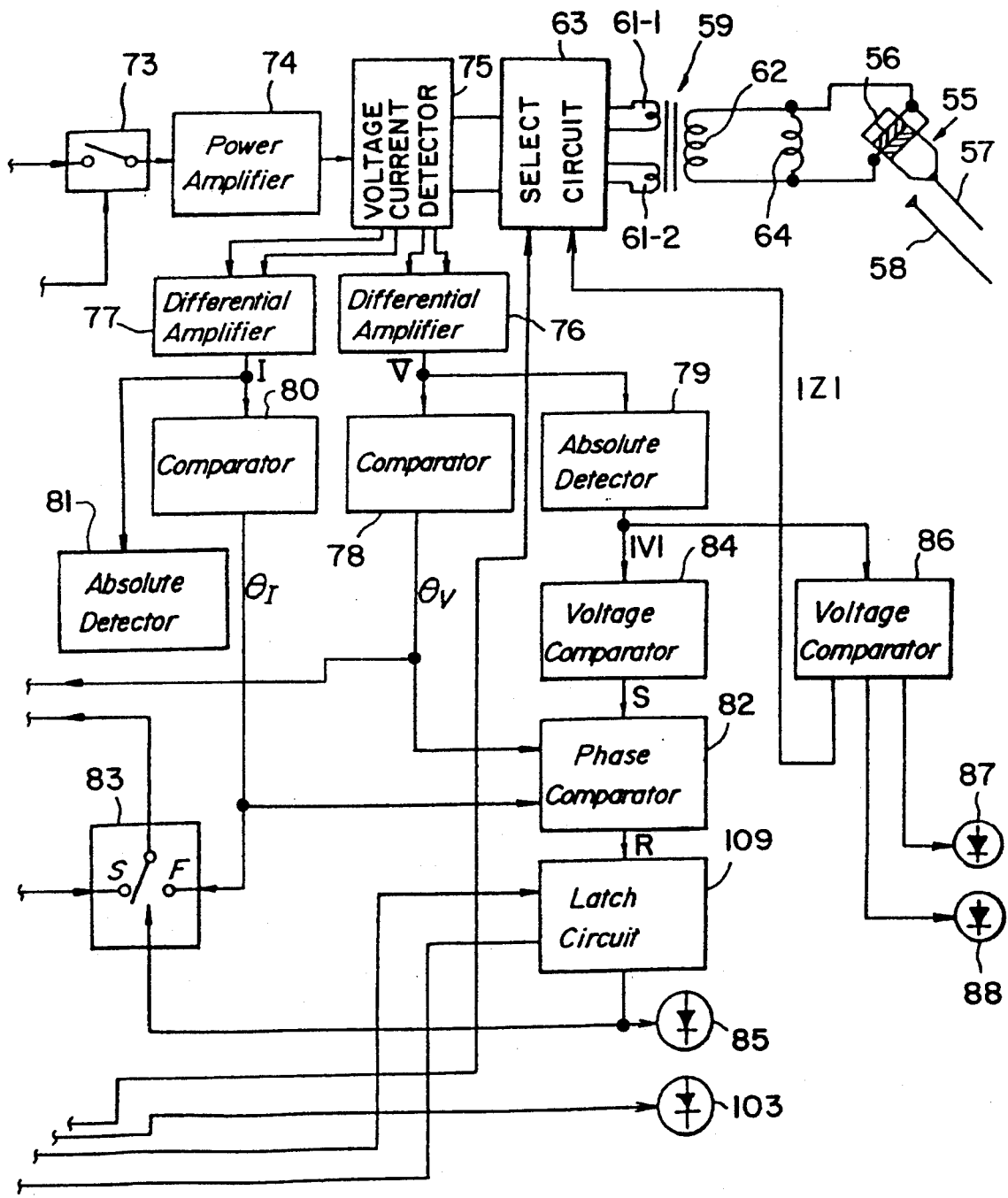

FIGS. 6A and 6B are a block diagram showing an embodiment of the ultrasonic surgical knife to which the ultrasonic oscillation generating apparatus according to the invention is applied. In the present embodiment, a hand piece 55 comprises an ultrasonic vibrating element 56 of Langevin type to which a short probe 57 and a long probe 58 having different impedance may be detachably secured. The ultrasonic vibrating element 56 is connected to a secondary side of a matching transformer 59 and is driven by the output of a phase lock loop (PLL) 60. The matching transformer 59 comprises two primary windings 61-1 and 61-2 and a secondary winding 62. In a similar manner to the embodiment shown in FIG. 2, the ratio of turns between the primary and secondary windings can be changed by a select circuit 63 including a relay and control circuit. Across the vibrating element 56 is connected an inductor 64 for canceling the damping capacitance of the element.

The phase lock loop 60 comprises a phase comparator (PC) 65, a charge pump 66 for converting the digital output of the phase comparator into the analog signal, a loop filter 67 and a voltage controlled oscillator (VCO) 68. The output of the charge pump 66 is applied to VCO 68 as the control voltage via the loop filter 67. The output of VCO 68 is supplied to the filter 69 as well as to a frequency divider 70, and the output of the frequency divider 70 is supplied to the filter 69, so that the rectangular output signal from VCO 69 is converted into a sinusoidal driving signal which contains only the resonance component of the ultrasonic vibrating element 56 to avoid unnecessary heat radiation from the element. In the present embodiment, the filter 69 is formed by a switched capacitor filter (SCF) whose cut-off frequency can be changed by an external clock input. When the filter is composed of such SCF, the amplitude variation and the phase rotation of the output signal of the filter can be removed, and therefore the constant current control and PLL are hardly affected by these variations so that the rectangular-sinusoidal conversion can be carried out in an ideal manner. Moreover, the impedance of the ultrasonic vibrating element 56 can be detected precisely during the frequency sweep of the driving signal, because only the fundamental wave is used.

The output of the filter 69 is supplied via voltage controlled amplifier (VCA) 71, buffer amplifier 72, switch circuit 73 and power amplifier 74 to the primary side of a matching transformer 59. By means of the matching transformer 59, it is possible to electrically isolate the circuit of the ultrasonic vibrating element 56 from the driving circuit and to attain the impedance matching between the power amplifier 74 and the ultrasonic vibrating element 56.

The voltage applied to the ultrasonic vibrating element 56 and the current flowing through the element are detected by a voltage and current detecting circuit 75 which includes voltage detecting potentiometer and current sensor which are similar to those shown in FIG. 2. The obtained voltage and current detection signals are supplied to differential amplifiers 76 and 77, respectively. In this manner the problem of in-phase noise which is inherent to the detection of the high voltage and large current can be effectively removed by means of the differential amplifiers 76 and 77. Furthermore, although the positive and negative terminals of the power amplifier 74 are connected inversely or the power amplifier is not a type whose one output terminal is not connected to the ground, the voltage and current detection signals can be obtained stably.

The voltage detection signal V generated from the differential amplifier 76 is supplied to a comparator 78 to detect a voltage phase detection signal $\theta_V$ as well as to an absolute value detecting circuit 79 to detect an absolute value of the amplitude of the detected voltage $|V|$. Similarly the current detection signal I produced by the differential amplifier 77 is supplied to as comparator 80 to derive a current phase detection signal $\theta_1$ as well as to the absolute value detecting circuit 81 to detect an absolute value of the detected current $|I|$.

Figure 7:
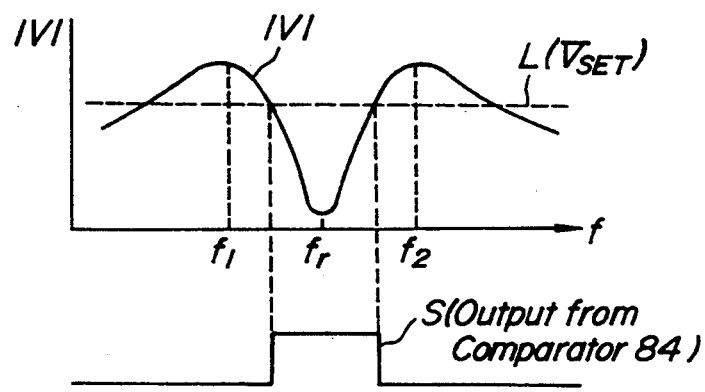
FIG. 7 is a graph representing the relationship between the frequency characteristic of the driving voltage and the output of the voltage comparator.

The voltage phase signal $\theta_V$ derived from the comparator 78 is supplied to a phase comparator 82 as well as to variable input terminal V of the phase comparator 65 of PLL 60. The current phase signal $\theta_I$ derived from the comparator 80 is supplied to the phase comparator 82 as well as to a contact F of a switching circuit 83. The absolute voltage signal $|V|$ derived from the absolute value detector 79 is supplied to a voltage comparator 84. The frequency characteristic of the absolute value of the voltage detection signal is shown in FIG. 7. In the voltage comparator 84, the absolute voltage value $|V|$ is compared with a predetermined threshold value L, and the voltage comparator produces an output signal S when the absolute value is smaller than the threshold value L. Since the driving circuit of the present embodiment operates in the constant current mode, the absolute value of the driving voltage represents the impedance of the ultrasonic vibrating element 56. When the voltage comparator 84 generates the signal S, the phase comparator 82 is enabled to detect the phase difference $\Delta\theta$ between the voltage phase signal $\theta_V$ and the current phase signal $\theta_I$. When the frequency of the driving signal becomes equal to the desired resonance frequency $f_r$ of the ultrasonic vibrating element 56, the phase difference $\Delta\theta$ becomes zero. Then, the phase comparator 82 generates a resonance detection signal R. This resonance detection signal R is supplied to a latch circuit 109 to change the state of the latch circuit 109. Then, the switching arm of the switching circuit 83 is changed from the contact S to the contact F and the current phase signal $\theta_I$ is supplied to the reference input terminal R of the phase comparator 65 and PLL 60 is operated in the feedback control mode in which the driving signal frequency is automatically controlled to follow the resonance frequency of the ultrasonic vibrating element 56. At the same time, a light emitting diode 85 is lit to denote that PLL 60 is driven into the feedback control mode. It should be noted that the output signal derived from the latch circuit 109 is also supplied to a control circuit 93. The function of this control circuit 93 will be explained in detail hereinafter.

FIG. 8 is a circuit diagram illustrating a detailed construction of the phase comparator 82 and voltage comparator 84. The phase comparator 82 includes three D-flip-flops (D-FF) 89, 90, 91 and an OR gate 92. The voltage phase signal $\theta_V$ generated from the phase comparator 78 is applied to D-input of the first D-FF 89 and the current phase signal $\theta_1$ generated from the phase comparator 80 is applied to clock input CK of D-FF 89. Q and Q outputs of this D-FF 89 are applied to clock input CK of D-FF 90 and clock input CK of D-FF 91, and Q outputs of these D-FFs 90 and 91 are applied to the OR gate 92. An output signal from the OR gate 92 is supplied to the latch circuit 109 as the resonance point detection signal R. To D inputs of D-FFs 90 and 91 are applied a supply source voltage $V_{CC}$. The voltage comparator 84 comprises a comparator IC 84a and the absolute voltage signal $|V|$ derived from the absolute value detector 79 is applied to an inverted input of the operational amplifier and a variable voltage source 84b is connected to the non-inverted input. A voltage set by the variable voltage source 84b represents the threshold level E shown in FIG. 7. An output signal from the operational amplifier 84a is applied to clear terminals CLR of D-FFs 90 and 91.

As illustrated in FIGS. 6A and 6B, the absolute current signal $|I|$ generated from the absolute value detector 81 is supplied to an inverted input of a differential amplifier 94. To a non-inverted input of the differential amplifier 94 is applied a preset signal generated from a current setting circuit 95. An output signal of the differential amplifier 94 is applied, via a limiter 96, to a control input terminal of the voltage controlled amplifier 71 to control the amplification factor thereof such that the ultrasonic vibrating element 56 is always driven by the predetermined current which is set by the current setting circuit 98. To the current setting circuit 95 are connected a first Variable resistor 97 for setting a higher driving current level and a second variable resistor 98 for adjusting a lower driving current level. The current setting circuit 95 is controlled by a control signal supplied from the control circuit 93 such that during the starting time period, the driving current is set to the lower current level and after PLL 60 has been driven into the feedback control mode, the driving current is increased into the higher current level. In the manner explained above, the absolute current value $|I|$ is compared with the preset voltage supplied from the current setting circuit 95 in the differential amplifier 94 and the amplification factor of VCA 71 is controlled by the difference therebetween to control the driving signal to be applied to the buffer amplifier 72 and power amplifier 74. Therefore, even when the impedance is varied due to the variation in the load to the hand piece 55, it is possible to drive the ultrasonic vibrating element 56 with the constant current having the value set by the current setting circuit 95, so that the vibration amplitude of the hand piece 55 can be maintained constant.

To the control circuit 93 is connected a trigger circuit 99 to generate a trigger signal under the control of the control circuit. The trigger signal is applied to a reference voltage generator 100 to generate a reference voltage signal having a sawtooth waveform. This sawtooth voltage signal is applied to an oscillator 101 formed by the voltage controlled oscillator to generate the reference signal $\theta_{ref}$ having the monotonously increasing frequency. The frequency range of the oscillator 101 is substantially identical with that of VCO 68 in PLL 60.

Figure 9:
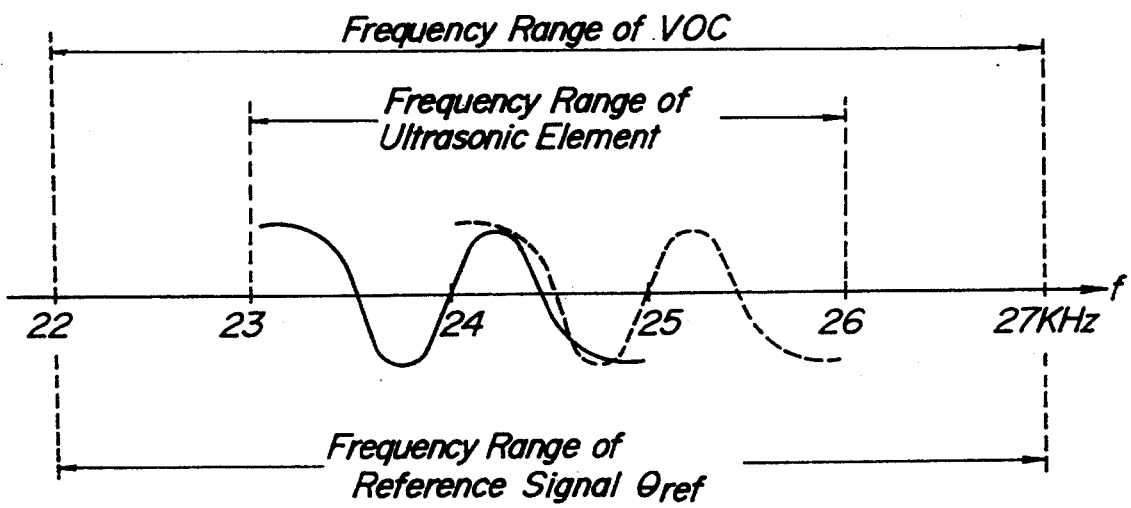
FIG. 9 is a graph showing the frequency range of the ultrasonic vibrating element and the oscillator.

FIG. 9 is a schematic view showing an example of the frequency ranges of the oscillator 101 and VCO 68. As shown in FIG. 9, the oscillator 101 and VCO 68 generate the signals whose frequency is varied from 22 KHz to 27 KHz. In FIG. 9 there are also illustrated the frequency and phase characteristics of two ultrasonic vibrating elements. It should be noted that these ultrasonic vibrating elements are designed to operate within a frequency range from 23 KHz to 26 KHz. In the starting period, the control circuit 93 sends a signal to the latch circuit 109 to reset it, and the switching circuit 83 is set by the latch circuit such that its switching arm is connected to the contact S. Therefore, the reference signal $\theta_{ref}$ is supplied to the reference input terminal R of the phase comparator 65 in PLL 60. The trigger signal generated by the trigger circuit 99 is also supplied to a counter 102 which counts the number of the trigger signals generated from the trigger circuit. When the counter 102 has counted a predetermined number of trigger signals, it produces an abnormal detection signal by means of which the switching circuit 73 is opened and a light emitting diode 103 is lit to indicate that any abnormal condition has occurred. It should be noted that the counter 102 is reset by a signal supplied from the control circuit 102 is reset by a signal supplied from the control circuit 93 when PLL 60 is changed from the sweep control mode to the feedback control mode.

The output signal from the loop filter 67 in PLL 60 is also supplied to a low pass filter (LPF) 104 to remove spike noise contained in the control voltage for VCO 68. The output or the low pass filter 104 is applied to a window comparator 105. In the window comparator 105, the control voltage for VCO 68 is compared with lower and upper threshold levels, these threshold levels being corresponding to the lower and upper frequencies of the frequency range of the voltage controlled oscillator 68 as well as of the oscillator 101. That is to say, in the present embodiment, the lower threshold level of the window comparator 105 corresponds to 23 KHz and the upper threshold level corresponds to 26 KHz as can be understood from the drawing of FIG. 9. When the control voltage becomes lower or higher than the lower or upper threshold levels, the window comparator 105 sends a reset signal to the control circuit 93. Then, the control circuit 93 sends a reset signal to the trigger circuit 99 to generate the trigger signal, and at the same time, the control circuit 93 sends a reset signal to the latch circuit 109 to reset its condition. Therefore, the reference signal $\theta_{ref}$ is generated from the oscillator 101 and the switching circuit 83 is driven to selectively supply the reference signal to the phase comparator 65 in PLL 60. If the above explained resetting means is not provided, the oscillation frequency of VCO 68 is decreased or increased up to the lowest or highest frequency when the frequency of the driving signal becomes out of the automatic resonance frequency tracking range. In the present embodiment, the out-of lock condition is detected by the window comparator 105 and as soon as the driving frequency becomes out of the frequency range of ultrasonic vibrating element 56, PLL 60 is changed into the sweep control mode. The control voltage applied to the control terminal of VCO 68 is smoothed to a certain extent by the loop filter 67, but when use is made of the edge trigger type phase comparator 65 and the loop filer must be designed to have the relatively high speed characteristic, so that the control voltage to be applied to VCO 68 might contain spike noise at edges of the two input signals to the phase comparator 65. This spike noise might affect the operation of the window comparator 105. In the present embodiment, such a spike noise can be removed by the low pass filter 104.

To the control circuit 93 there are further connected a foot switch 106, a suction unit 107 for sucking body tissues cut by the ultrasonic surgical knife, and a water supply unit 108 for cooling the probe 57 coupled with the hand piece 55 as well as for washing the cut portion of the body.

The absolute value of the $|V|$ of the voltage detection signal supplied from the absolute value detecting circuit 79 is also supplied to a voltage comparator 86 and is compared with a predetermined preset value to detect the impedance $|Z|$. The output of the voltage comparator 86 is used to selectively operate either one of light emitting diodes 87 and 88 which represent the short probe and the long probe, respectively. The output of the voltage comparator 86 is also used to control the matching switch operation in the select circuit 63. It should be noted that the above mentioned preset value in the voltage comparator 86 is determined such that the short probe 57 can be distinguished from the long probe 58 in a reliable manner.

Now the operation of the ultrasonic surgical knife according to the present embodiment will be explained in detail.

As long as the foot switch 106 is made off, the switch 73 is opened and the switching circuit 83 is driven such that the switching arm is connected to the contact S so that the reference signal generated from the oscillator 101 will be supplied to the reference input terminal R of the phase comparator 65 in PLL 60.

When the operator pushes down the foot switch 106 with his or her foot to enter the start signal to the control circuit 93, the control circuit resets the latch circuit 109 and counter 102 and sends the selection signal to the current setting circuit 95 to select the lower constant current setting variable resistor 98, so that the current setting circuit applies the low current setting voltage to the differential amplifier 94. At the same time, the control circuit 93 sends the control signal to the switch 73 so that the switch is closed. Furthermore, the control circuit 93 supplies the reset signal to the trigger circuit 99 to generate the trigger signal. Then, the reference voltage generator 100 starts to generate the sawtooth shape reference voltage and the oscillator 101 starts to generate the reference signal $\theta_{ref}$ having the frequency which is increased linearly. This reference signal $\theta_{ref}$ is supplied to the reference input terminal R of the phase comparator 65 by means of the switching circuit 83. At the same time, the voltage phase signal $\theta_V$ generated from the comparator 78 is applied to the variable input terminal V of the phase comparator 65. After the phase lock loop 60 has been driven into the phase lock condition, it operates to sweep the driving frequency in accordance with the linearly varying frequency of the reference signal $\theta_{ref}$.

As explained above, in the sweep control mode, the current setting circuit 68 operates to generate the lower current setting voltage, so that the amplitude of current of the driving signal is maintained to the predetermined lower level. The impedance of ultrasonic vibrating element 36 is proportional to the voltage of the driving signal, because the ultrasonic element is driven under the constant current mode. The variation of the driving signal voltage is detected by the voltage-current detecting circuit 75, differential amplifier 76 and absolute value detector 79 and is monitored in the voltage comparator 84 and is compared with the predetermined threshold level L. The absolute voltage value $|V|$ is also supplied to a voltage comparator 86 and is compared therein with a predetermined value to detect the probe 57 connected to the hand piece 55. During the first scan the output signal from the voltage comparator 86 is supplied to the select circuit 63 to change the connection of the primary windings 61-1 and 61-2 of the matching transformer 59, In this manner the output impedance of the driving circuit is matched to the impedance of the ultrasonic transducer having the hand piece 55 including the ultrasonic vibrating element 56 and the probe 57 coupled to the hand piece. At the same time, one of light emitting diodes 87 and 88 is lit to indicate the probe 57 coupled to the hand piece 55.

During the second scan, when the absolute value of the driving voltage $|V|$ becomes smaller than the threshold level $V_{SET}$, i.e. the impedance of the ultrasonic vibrating element 56 is reduced lower than the predetermined value, the enabling signal S is supplied to the phase comparator 82 and the phase comparator is allowed to compare the phases of the voltage and current phase signal $\theta_V$ and $\theta_1$ with each other. When the driving signal becomes in-phase with the resonance vibration of the ultrasonic vibrating element 56, the phase difference between these signals becomes zero and the phase comparator 82 generates the resonance point detection signal R. Then, the latch circuit 109 is set by this signal and the output signal of the latch circuit 109 is supplied to the switching circuit 83 to change the switching arm from the contact S to the contact F, so that PLL 60 is driven to operate in the feedback control mode. At the same time, the light emitting diode 85 is lit by the output of the latch circuit 109. The latch circuit 109 also sends, to the control circuit 93, the signal which represents that the driving frequency has been locked with the desired resonance frequency $f_r$ of the ultrasonic vibrating element 56. In response to this, the current setting circuit 95 is controlled to select the higher current setting variable resistor 97 and the higher current level setting voltage is applied to the differential amplifier 94, so that the current of the driving signal is adjusted to the predetermined higher level. Since PLL 60 operates in the feedback control mode, the frequency of the driving signal is automatically adjusted to the resonance frequency $f_r$ of the ultrasonic vibrating element 56. When PLL 60 is driven into the feedback control mode, the control circuit 93 supplies the control signals to the suction unit 107 and water supply unit 108 and the desired operation is performed. Since this operation has been known in the relevant art of technique, its detailed explanation is dispensed with. The above operation is continued until the foot switch 106 is made off. It should be noted that the transfer into the resonance point tracking mode is effected even if the impedance change is not carried out by the select circuit 63 during the first scan.

If the resonance point is not found during the second frequency sweep, the frequency of the output oscillation of VCO 68 will be increased up to the maximum frequency of 27 KHz or will be decreased to the lowest frequency of 22 KHz of the frequency range of VCO 68 and oscillator 101. In the present embodiment, the frequency control voltage produced from the loop filter 67 in PLL 60 is monitored by the window comparator 105, and when this voltage becomes higher than the upper threshold value corresponding to the maximum frequency of 26 KHz or the minimum frequency of 22 KHz of the frequency range of the ultrasonic vibrating element 56, the window comparator 105 supplies the reset signal to the control circuit 93, so that the trigger circuit 99 is driven again. Then, the oscillator 101 restarts the generation of the reference signal $\theta_{ref}$ having the varying frequency to effect the frequency sweep again. In this manner, the frequency sweep operation is repeated until the driving signal is locked with the resonance frequency of the ultrasonic vibrating element. The number of the reset operations is counted by the counter 102, and if the count value reaches a predetermined value such as ten, the switch 73 is forcedly made off and the light emitting diode 103 is lit to indicate that the driving signal could not be locked with the resonance frequency of the ultrasonic vibrating element 56. Then, the operator can know that any abnormal condition has occurred in the hand piece 55. In this manner, it is possible to avoid any danger which might be produced when the ultrasonic vibrating element 56 is continued to be driven under the abnormal condition.

According to the ultrasonic surgical knife explained above, the kind of the probe coupled with the hand piece can be automatically detected and the impedance matching is effected also automatically, so that the hand piece can be driven always efficiently. Furthermore, the ultrasonic transducer can be positively driven into the resonance point tracking mode, and even if the tracking mode is lost, it is possible to effect the restart. Moreover, the abnormal condition of the hand piece 55 can be detected. In the present embodiment, there is provided the constant current driving circuit, and thus the ultrasonic vibrating element can be driven at the constant amplitude and the frequency characteristics of impedance can be detected in a simple manner, so that the resonance point can be detected accurately and positively. Further the voltage applied to the ultrasonic vibrating element 56 and the current passing through the element are detected in the differential manner, so that the in-phase noise can be removed effectively and the desired voltage and current can be detected in regardless of the output type of the power amplifier 74. Therefore, the high tension circuitry surrounding the power amplifier can be floated with respect to the ground and the leakage current to the ground in the circuit of the ultrasonic transducer can be reduced to a large extent.

Figure 10:
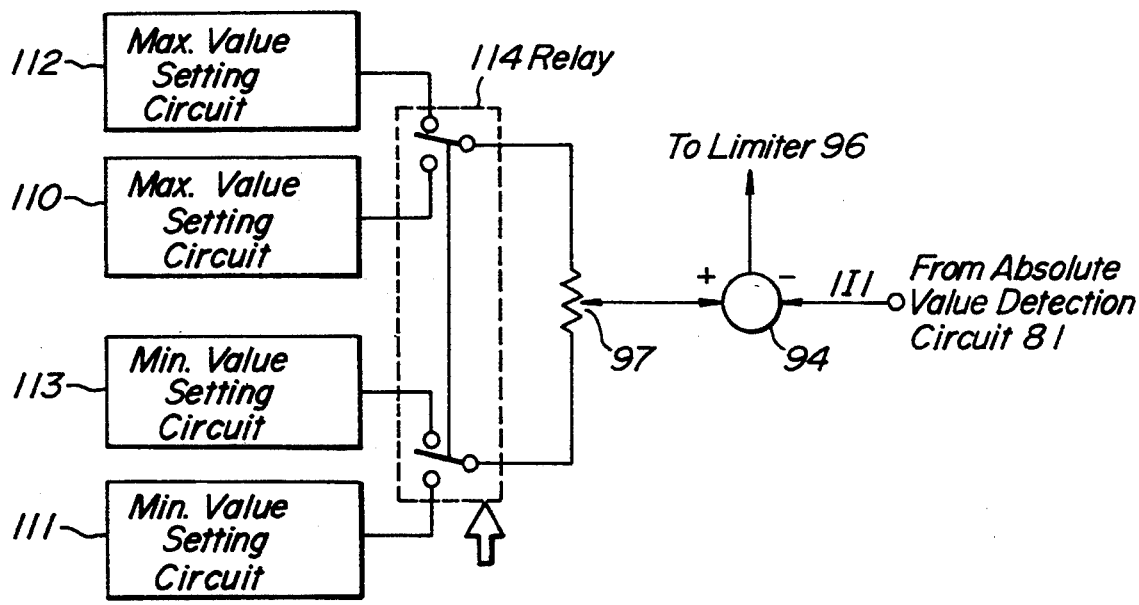
FIG. 10 is a block diagram illustrating a third embodiment of the apparatus according to the invention.

It should be noted that the voltage applied to the ultrasonic vibrating element and the current flowing through the element are detected on the primary side of the matching transformer 59, out they nay be detected on the secondary side of the matching transformer. Further, the amplitude which is adjusted by means of the variable resistor 97 in the current setting circuit 95 may be set by other means. For instance, as shown in FIG. 10, there may be provided maximum and minimum value setting circuits 110 and 111 for the short probe 57 and maximum and minimum value setting circuits 112 and 113 for long probe 58 and these circuits may be selected by a relay 114 in accordance with the output of the voltage comparator 86. In this modified embodiment, the probes 57 and 58 may have different withstanding properties.

Figure 11:
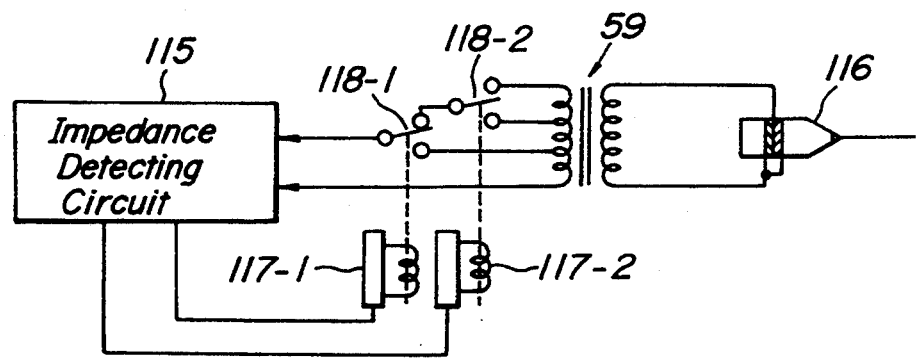
FIG. 11 is a block diagram depicting a fourth embodiment of the apparatus according to the invention.

In the above explained embodiment, the impedance of two probes 57 and 58 is detected and the output impedance of the driving circuit is adjusted in accordance with the detected probe. According to the present invention, more than two probes may be detected to attain the proper impedance matching. In this case, there are arranged more than two taps on the primary side of the matching transformer 59 as shown in FIG. 11. These taps may be selected by relays 117-1 and 117-2 in accordance with the impedance of the ultrasonic vibrating element, detected by an impedance detecting circuit 115.

In order to protect the relay contacts for changing the primary windings of the matching transformer 59, the voltage applied to the ultrasonic vibrating element 56 is reduced to zero upon the switching as explained before with reference to FIG. 3. It is also possible to insert a spark killer formed by CR circuit which does not affect within the driving frequency range between the contacts of the relay. Moreover, not only attain the impedance matching but also the frequency of the driving signal, an amount of supply water and so on may be changed in accordance with the detected impedance of the ultrasonic vibrating element. Further, the present invention may be equally applied to various kinds of ultrasonic devices such as ultrasonic working machine other than the ultrasonic surgical knife.

The present invention also relates to the ultrasonic oscillation generating apparatus in which the ultrasonic vibrating element can be driven stably and safely without breaking the driving circuit and ultrasonic vibrating element and subjecting the living body to danger. In the ultrasonic oscillation generating apparatus according to the invention, in order to attain the above object, there is provided a limiter for limiting the maximum amplification factor of the voltage controlled amplifier which is controlled in accordance with the driving current.

Figure 12:
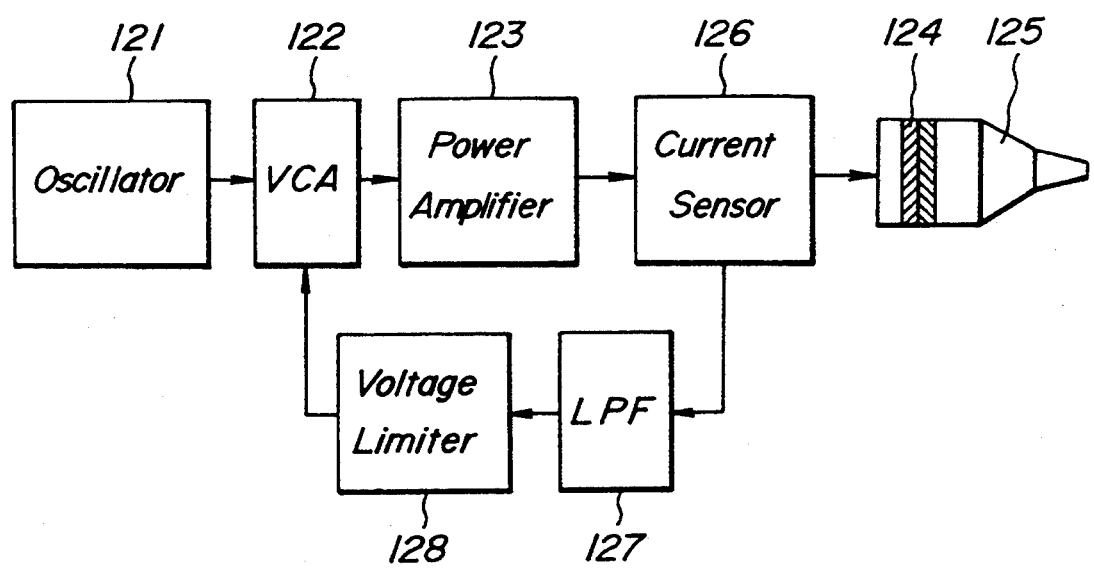
FIG. 12 is a block diagram showing the basic construction of the ultrasonic oscillation generating apparatus according to the invention, in which the amplitude of the driving signal is limited.

FIG. 12 is a block diagram showing the basic construction of the ultrasonic oscillation generating apparatus according to the present invention, in which the maximum amplification factor is limited. An output of an oscillator 121 is supplied to a voltage controlled amplifier (VCA) 122 whose amplification factor can be varied. The output of VCA 122 is amplified by a power amplifier 123 and is then supplied to an ultrasonic vibrating element 124. The ultrasonic vibration produced by the ultrasonic vibrating element 124 is transmitted to a probe 125. A current passing through the ultrasonic vibrating element 125 is detected by a current detector 126 and an output of the current sensor is supplied via low pass filter (LPF) 127 and voltage limiter 128 to VCA 122 as the amplification factor control signal.

Figure 13:
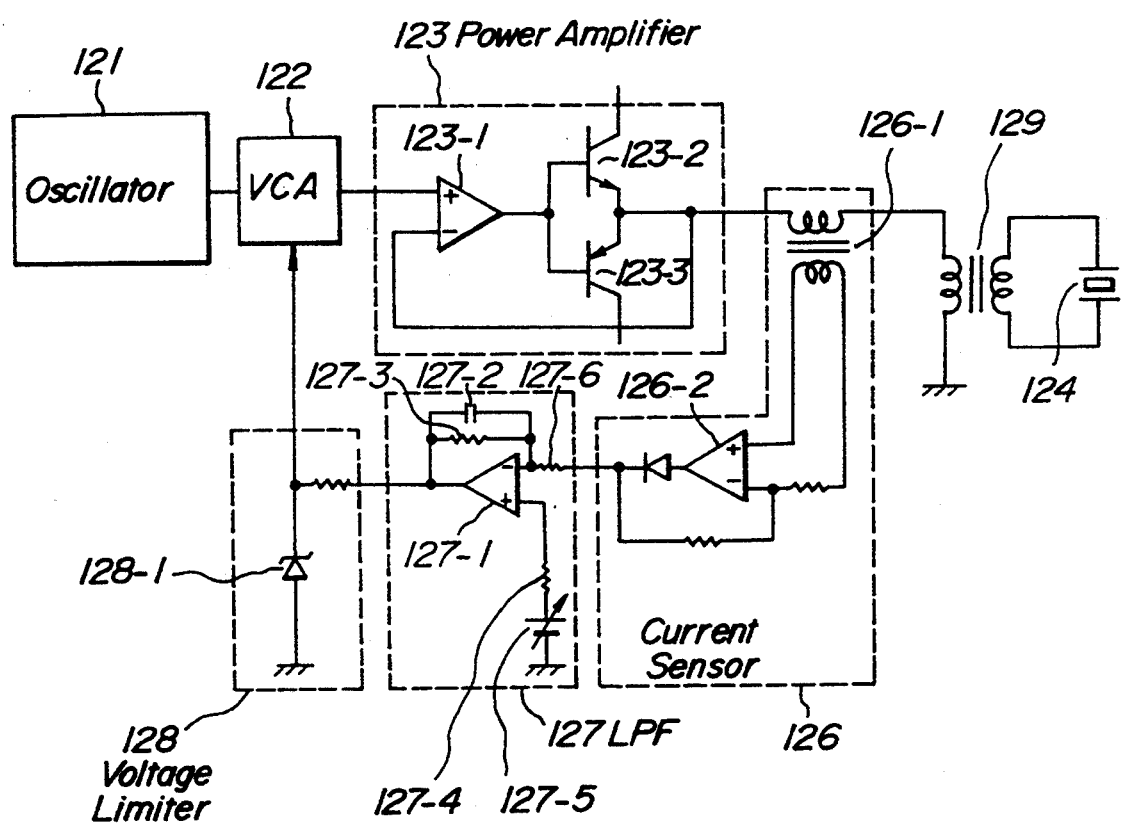
FIG. 13 is a block diagram showing an embodiment of the apparatus according to the invention.

FIG. 13 is a circuit diagram illustrating, the detailed construction of a major part of the apparatus shown in FIG. 12. The power amplifier 123 comprises a differential amplifier 123-1 and a push-pull amplifier having two transistors 123-2 and 123-3. To inputs of the differential amplifier 123-1 are supplied the output of the oscillator 121 and the output of the power amplifier 123, and the output of the differential amplifier 123-1 is supplied to the bases of the transistors 123-2 and 123-3. The output of the power amplifier 123 is derived from the commonly connected emitters of the transistors 123-2 and 123-3 and is supplied via a matching transformer 129 to the ultrasonic vibrating element 124. The current sensor 126 comprises a transformer 126-1 and a differential amplifier 126-2 for detecting the absolute value of the output of the transformer 126-1. The output of the differential amplifier 126-1 is supplied to LPF 127.

The low pass filter 127 comprises a differential amplifier 127-1 to whose inverted input is supplied output of the differential amplifier 126-2 via a resistor 127-6, a capacitor 127-2 and a resistor 127-3 connected in parallel with each other across the terminal and the non-inverted input terminal of the differential amplifier 127-1, and a variable reference voltage supply source 127-5 connected to the non-inverted input terminal of the differential amplifier 127-1 via a resistor 127-4. The reference voltage supply source 127-5 is provided for setting the driving current for the ultrasonic vibrating element to a given level. The output of the differential amplifier 127-1 is supplied to the voltage limiter 128.

The voltage limited 128 includes a zener diode 128-1 having a given threshold voltage which limits the maximum level of the output voltage of the limiter 128 so that the maximum amplification factor of VCA 122 can be limited by the threshold voltage of the zener diode 128-1. That is to say, the amplification factor of VCA 122 can be adjusted within a range below the maximum level such that the driving current for the ultrasonic vibrating element is made identical with the value set by the reference voltage supply source 127-5 in LPF 127.

By constructing the apparatus as explained above, even if the driving current for the ultrasonic vibrating element 124 is reduced to a great extent and the output of LPF 127 is varied largely in accordance with the change in the electric property of the ultrasonic vibrating element due to the variation of the object to which the tip of the probe 125 is urged, the amplification factor of VCA 122 is not increased extraordinarily, because the control voltage for VCA 122 is limited by the voltage limiter 128. Therefore, the driving circuit and ultrasonic vibrating element can be effectively prevented from being applied extraordinarily high voltages which might cause the breakage of these parts. Further, the patient can be protected against the danger and injure, and the ultrasonic vibrating element 124 can be operated stably and safely.

Figure 14:
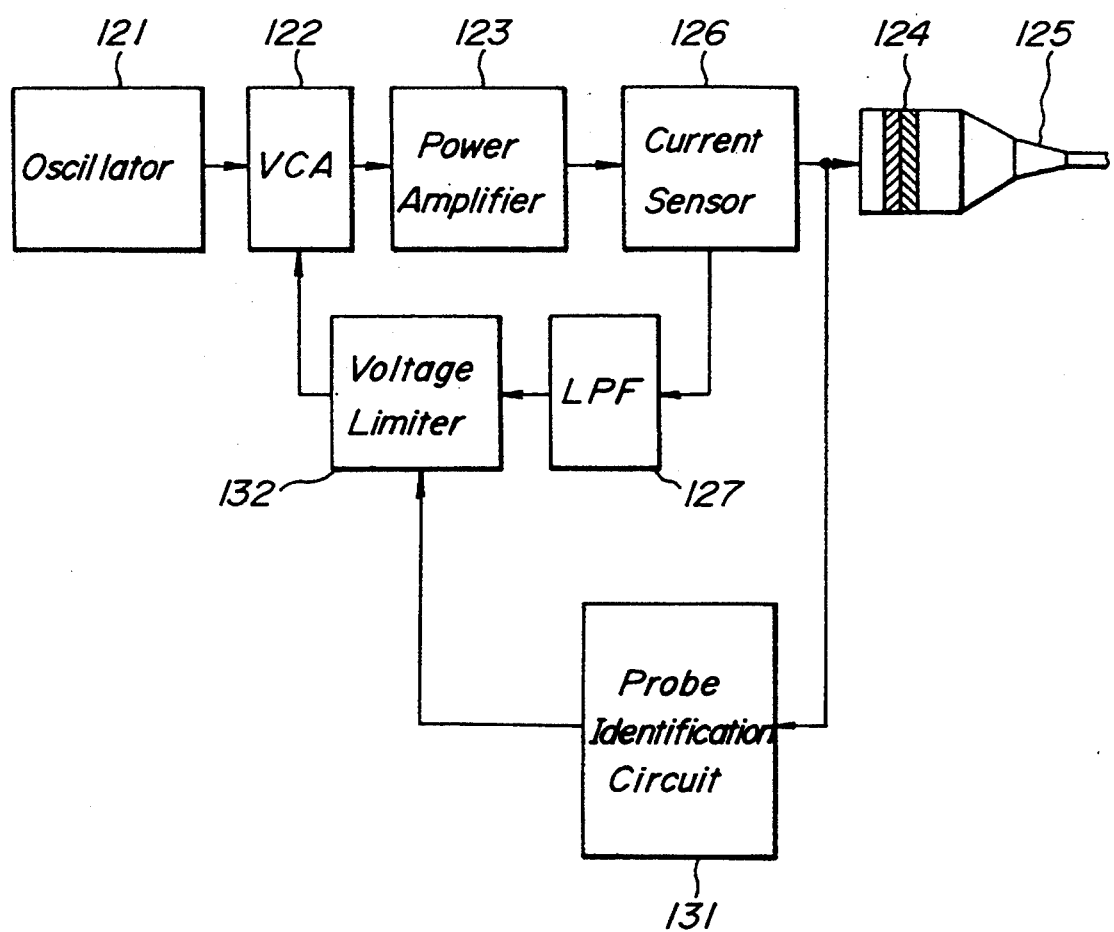
FIG. 14 is a block diagram illustrating another embodiment of the apparatus according to the invention.

FIG. 14 is a block diagram depicting another embodiment of the ultrasonic oscillation generating apparatus according to the present invention. In this embodiment, the impedance of the probe 125 detachably coupled with the ultrasonic vibrating element 124 is detected by a probe identification circuit 131 for detecting a kind or type of the probe 125 in accordance with the impedance of the ultrasonic vibrating element 124 and the maximum amplification factor of VCA 122 is adjusted by a voltage limiter 132 which is constructed to change the threshold value. The remaining construction of the apparatus according to the present invention is the same as the embodiment shown in FIG. 13.

Figure 15:
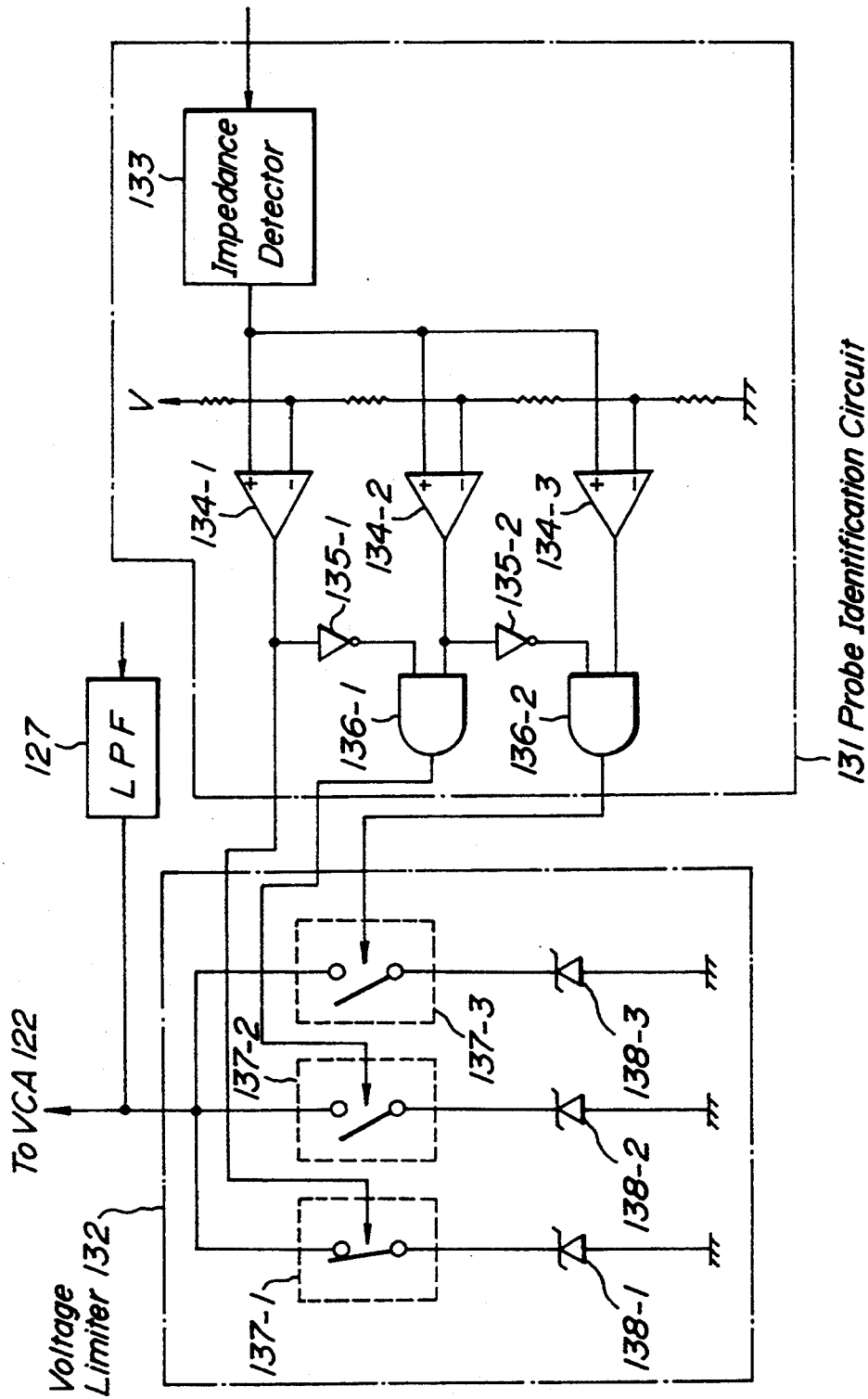
FIG. 15 is circuit diagram showing the detailed construction of a major part of the apparatus.

FIG. 15 is a circuit diagram showing the detailed construction of the probe identification circuit 131 and voltage limiter 132 shown in FIG. 13. The probe identification circuit 131 comprises an impedance detecting circuit 133 for detecting the impedance of the probe 124, comparators 134-1 to 134-3 whose positive input terminals are connected to the output terminal of the impedance detecting circuit 133 and whose negative input terminals are connected to a supply source voltage V, NOT gates 135-1 and 135-2 and AND gates 136-1 and 136-2. In the present embodiment, the ultrasonic vibrating element is driven by the constant current, so that the impedance detecting circuit 133 may be composed of a voltage detecting circuit. The voltage limiter 132 comprises three switches 137-1 to 137-3 connected in parallel with each other, and three zener diodes 138-1 to 138-3 connected in series with respective switches. It should be noted that the zener diodes 138-1 to 138-3 have different threshold voltages. When the impedance of the ultrasonic vibrating element is high, all the comparators 134-1 to 134-3 produce outputs, so that the AND gates 136-1 and 136-2 do no generate the outputs. Therefore, only the switch 137-1 is closes and the zener diode 138-1 is connected to the output terminal of LPF 127. When the impedance of the ultrasonic vibrating element is low, only the comparator 134-3 generates the output, so that only the switch 137-3 is closed and the zener diode 138-3 is connected to LPF 127. When the ultrasonic vibrating element has the impedance which is between said high and low values, the comparators 134-2 and 134-3 produce the output and the AND gate 136-1 actuates the switch 137-2 and the zener diode 138-2 is connected to LPF 127. In this manner, the maximum voltage applied to the control terminal of VCA 122 can be changed in accordance with the impedance of the ultrasonic vibrating element.

FIG. 16 is a side view showing the detailed construction of the hand piece and the probe coupled thereto. The ultrasonic vibrating element 143 is secured to a main body 142 of the hand piece 141. To the main body 142 is secured a hone 144 for amplifying the vibration of the ultrasonic vibrating element and a flexible tube 145 is connected to the hone. Within the tube 145, there is formed a conduit 146 which is communicated with a suction tube 147 via the hand piece 141. The tube 145 is installed in a flexible insertion tube 148 of the endoscope. At the proximal end of the insertion tube 148 are provided a handle section 149 and a slider 150, and the tube 145 is secured to the slider 150. The slider 150 is biased by a spring 151 to move away from the handle section 149. By moving the slider 150 toward the handle section 149 against the force of the spring 151, the distal end of the tube 145 is protruded from the tip of the insertion tube 148 and is brought into contact with the tissues of a body to be processed. Within the insertion tube 148, there is also arranged an optical observing device including light guide optical fiber bundle, objective lens system and image guide optical fiber bundle, and an eye piece 152 coupled with the image guide fiber bundle is provided at the proximal end of the insertion tube 148.

By using the above explained apparatus, the object to be processed is observed by the endoscope and the tip of probe 145 is urged against the object, and then the ultrasonic vibrating element 143 is driven to produce the ultrasonic oscillation. The object is broken by the ultrasonic vibration into pieces and the tissues are taken out of the patient body by means of the conduit 146.

It should be noted that the present invention can be applied not only the above explained ultrasonic suction apparatus, but also the ultrasonic surgical knife and ultrasonic working apparatuses.

Further, in the embodiments so far explained the kind of the probe coupled with the ultrasonic vibrating element is identified by detecting the impedance of the probe. However, according to the invention the probe may be identified by various methods. For instance, the shape of the base portion of the probe which is coupled with the front end portion of the ultrasonic vibrating element may be changed in accordance with the kind of the probe and this shape of the end portion of the probe may be detected by detecting resistors arranged on the front end surface of the ultrasonic vibrating element or an optically readable member such as a bar code and a means for detecting or reading the shape or the mark may be provided in the front end portion of the ultrasonic vibrating element.

As explained in detail, in the ultrasonic oscillation generating apparatus according to the present invention, since there is provided the means for limiting the upper threshold value of the amplification factor of the voltage controlled amplifier which is controlled on the basis of the driving current for the ultrasonic vibrating element, even if the electrical property of the ultrasonic vibrating element is changed to a great extent and the signal for controlling the amplification factor of the voltage controlled amplifier is increased extraordinarily, the amplification factor is restricted to the predetermined maximum value so that the voltage applied to the ultrasonic vibrating element is not increased and the driving circuit and the ultrasonic vibrating element can be protected effectively. Further the object to be processed can be effectively prevented from being injured to be processed can be effectively prevented from being injured and the ultrasonic vibrating element can be driven stably and safely.

What is claimed is:

1. An apparatus for generating an ultrasonic oscillation comprising:
   an ultrasonic transducer having an ultrasonic vibrating element which produces an ultrasonic oscillation and a probe which transmits the oscillation produced by the ultrasonic vibrating element, said ultrasonic transducer having an impedance;

a driving circuit which supplies a driving power to said ultrasonic vibrating element, said driving circuit having an output impedance;

an impedance matching means connected between said ultrasonic transducer and said driving circuit for matching the output impedance of the driving circuit to the impedance of said ultrasonic transducer;

a probe identifying means for identifying a kind of said ultrasonic transducer to generate a probe identification signal; and controlling means for automatically controlling said impedance matching means in accordance with said probe identification signal supplied from said probe identifying means such that the output impedance of said driving circuit is matched to the impedance of said ultrasonic transducer.

2. An apparatus according to claim 1, wherein said impedance matching means comprises a matching transformer having a plurality of primary windings and a secondary winding connected to the ultrasonic transducer, a switching circuit which selectively connects one of said primary windings into the circuit, and a control circuit which controls said switching circuit in accordance with said probe identification signal supplied from said probe identifying means such that the output impedance of said driving circuit is matched with the impedance of the ultrasonic transducer.

3. An apparatus according to claim 2, wherein said switching circuit comprises a relay driven by said control circuit.

4. An apparatus according to claim 1, wherein said probe identifying means comprises a circuit which detects the impedance of said ultrasonic transducer to generate said probe identification signal.

5. An apparatus according to claim 4, wherein said circuit which detects the impedance of the ultrasonic transducer is constructed to detect the impedance of the ultrasonic transducer by detecting a voltage of said driving power.

6. An apparatus according to claim 5, wherein said circuit which detects the voltage of the driving power to detect the impedance of the ultrasonic transducer is provided on an input side of said impedance matching means.

7. An apparatus according to claim 6, wherein said probe identifying means comprises a voltage detection circuit which detects an absolute value of the voltage of said driving power, a plurality of comparators whose outputs are inverted when the absolute value of the detected voltage exceeds different reference voltages, and a logic circuit which generates said probe identification signal in accordance with conditions of the outputs of said comparators.

8. An apparatus according to claim 1, wherein said ultrasonic transducer is constructed such that said probe includes a base portion which is detachably coupled with a front end portion of said ultrasonic vibrating element, and said probe identifying means comprises a first means provided in said base portion of the probe for identifying the kind of the probe and a second means provided in said front end portion of the ultrasonic vibrating element for detecting the kind of the probe in co-operation with said first means.

9. An apparatus for generating an ultrasonic oscillation comprising:

an ultrasonic transducer having an ultrasonic vibrating element which produces an ultrasonic oscillation and a probe which transmits the oscillation produced by the ultrasonic vibrating element;

a driving circuit having a voltage controlled amplifier which supplies a driving power to said ultrasonic vibrating element;

a feedback loop connected between ultrasonic transducer and said driving circuit which detects a current of said driving power supplied to said ultrasonic transducer and applies a control voltage corresponding to said current of the driving power to said voltage controlled amplifier to control an amplification of the voltage controlled amplifier to thereby maintain said current of said driving power supply at a constant level; and a voltage limiting means connected in said feedback loop for limiting an amplitude of said control voltage.

10. An apparatus according to claim 9, wherein said feedback loop comprises a current detector connected between said driving circuit and said ultrasonic transducer, a current-voltage converter which converts a current detected by said current detector into a voltage, and a low pass filter which passes a low frequency component of the voltage output from the converter, whereby an output signal from the low pass filter is supplied to said voltage limiting means.

11. An apparatus according to claim 10, wherein said current detector includes a current transformer having a primary winding connected in a line which supplies the driving power to the ultrasonic transducer and a secondary winding which produces the driving current, and said current-voltage converter includes a differential amplifier having positive and negative input terminals connected across said secondary winding.

12. An apparatus according to claim 9, wherein said voltage limiting means comprises at least one zener diode.

13. An apparatus for generating an ultrasonic oscillation comprising:

an ultrasonic transducer having an ultrasonic vibrating element which produces an ultrasonic oscillation and a probe which transmits the oscillation produced by the ultrasonic vibrating element;

a driving circuit having a voltage controlled amplifier which supplies a driving power to said ultrasonic vibrating element;

a feedback loop connected between said ultrasonic transducer and said driving circuit which detects a current of said driving power supplied to said ultrasonic transducer and applies a control voltage corresponding to said current of the driving power to said voltage controlled amplifier to control an amplification of the voltage controlled amplifier to thereby maintain said current of said driving power supply at a constant level;

a voltage limiting means having a plurality of voltage limiting elements connected in said feedback loop for limiting an amplitude of said control voltage;

probe identifying means for identifying a kind of said ultrasonic transducer to generate a probe identification signal; and controlling means for automatically switching said plurality of voltage limiting elements of the voltage limiting means in accordance with the probe identification signal produced by the probe identifying means.

14. An apparatus according to claim 13, wherein said probe identifying means comprises an impedance detection circuit which detects an impedance of said ultrasonic transducer to generate the probe identification signal for identifying the kind of the ultrasonic transducer.

15. An apparatus according to claim 13, wherein said impedance detection circuit is constructed to detect a voltage of the driving power for the ultrasonic transducer.

16. An apparatus according to claim 15, wherein said probe identifying means comprises a voltage detection circuit which detects an absolute value of the voltage of said driving power, a plurality of comparators whose outputs are inverted when the absolute value of the detected voltage exceeds different reference voltages, and a logic circuit which generates said probe identification signal in accordance with conditions of the outputs of said comparators.

17. An apparatus according to claim 13, wherein said plurality of voltage limiting elements are formed by zener diodes having different threshold voltages, and said controlling means comprises a plurality of switches which are driven by the probe identification signal supplied from said logic circuit, each of said zener diodes being connected to a respective one of said switches.

18. An apparatus for use in driving an ultrasonic surgical knife, wherein a plurality of probes having different impedances are selectively detachably coupled with said apparatus, said apparatus comprising:
an ultrasonic vibrating element, having a selected one of said plurality of probes coupled thereto, which applies an ultrasonic vibration to said selected probe;
an electric power supply source means for supplying a constant current to said ultrasonic vibrating element to vibrate the element;
a matching means provided between said ultrasonic vibrating element and said electric power supply source means for effecting impedance matching therebetween and including at least two transformers having different winding ratios;
a probe identifying means for detecting a voltage applied to said matching means to identify a kind of said selected probe coupled with the ultrasonic vibrating element; and
a switching means coupled with said matching means for selecting one of said transformers on the basis of an output signal supplied from said probe identifying means, said one of said transformers being suitable for the selected probe.

19. An apparatus according to claim 18, wherein said apparatus further comprises a display means for displaying the kind of the selected probe which has been identified by said probe identifying means.

20. An apparatus according to claim 18, wherein said electric power supply source means is constructed to have a first operation mode in which a low constant current is generated during a time in which the kind of the selected probe is identified and a second operation mode in which the ultrasonic surgical knife is driven.

21. A method of driving an ultrasonic vibrating apparatus comprising an ultrasonic vibrating element which applies an ultrasonic vibration to a probe coupled to the ultrasonic vibrating element, an electric power supply source means for supplying a constant current to said ultrasonic vibrating element to vibrate the ultrasonic vibrating element, a matching means provided between said ultrasonic vibrating element and said electric power supply source means for effecting impedance matching therebetween and including at least two kinds of impedance members, a probe identifying means for identifying a kind of the probe coupled with the ultrasonic vibrating element, and a switching means coupled with said matching means for selecting one of said impedance members on the basis of an output signal supplied from said probe identifying means, said one of said impedance members being suitable for the probe, comprising the steps of:
supplying a low current from said electric power supply source means for a time period during which the kind of the probe coupled with the ultrasonic vibrating element is identified;
operating said switching means, after the kind of the probe has been identified, to select said one of said impedance members which is suitable for the probe; and
supplying a high constant current from said electric power supply source means to drive the ultrasonic vibrating element to generate an ultrasonic vibration.

22. A method according to claim 21, wherein said probe identifying means includes a voltage comparing means for detecting a voltage of the electric power supply source means and comparing the voltage thus detected with a predetermined voltage, and said step of identifying the kind of the probe is carried out by detecting and comparing the voltage of the electric power supply source means with said predetermined voltage.

* * * * *